(12) United States Patent
Mundschau et al.

(10) Patent No.: US 7,700,530 B2
(45) Date of Patent: Apr. 20, 2010

(54) POLYSENSORIAL PERSONAL CARE CLEANSER COMPRISING A QUATERNARY SILICONE SURFACTANT

(75) Inventors: Stacy Averic Mundschau, Weyauwega, WI (US); Lisa Ann Flugge-Berendes, Appleton, WI (US); Scott W. Wenzel, Neenah, WI (US); Uyen TuongNgoc Lam, Appleton, WI (US); Corey Thomas Cunningham, Larsen, WI (US)

(73) Assignee: Kimberly Clark Worldwide, Inc., Neenah, WI (US)

( * ) Notice: Subject to any disclaimer, the term of this patent is extended or adjusted under 35 U.S.C. 154(b) by 3 days.

(21) Appl. No.: 12/164,999

(22) Filed: Jun. 30, 2008

(65) Prior Publication Data

US 2009/0325837 A1 Dec. 31, 2009

(51) Int. Cl.
*C11D 9/36* (2006.01)
*C11D 1/62* (2006.01)
*C11D 3/14* (2006.01)

(52) U.S. Cl. .................. 510/139; 510/119; 510/122; 510/123; 510/130; 510/157; 510/236; 510/268; 510/295; 510/304; 510/343; 510/347; 510/368; 510/371; 510/395; 510/400; 510/407; 510/466; 510/504

(58) Field of Classification Search .................. 510/119, 510/122, 123, 130, 157, 139, 236, 268, 295, 510/304, 343, 347, 368, 371, 395, 400, 407, 510/466, 504
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,100,324 A | 7/1978 | Anderson et al. | |
| 4,340,563 A | 7/1982 | Appel et al. | |
| 5,213,881 A | 5/1993 | Timmons et al. | |
| 5,284,703 A | 2/1994 | Everhart et al. | |
| 5,350,624 A | 9/1994 | Georger et al. | |
| 5,364,382 A | 11/1994 | Latimer et al. | |
| 5,486,166 A | 1/1996 | Bishop et al. | |
| 5,490,846 A | 2/1996 | Ellis et al. | |
| 6,287,580 B1 * | 9/2001 | Gott et al. | 424/401 |
| 6,306,412 B1 * | 10/2001 | Crotty et al. | 424/402 |
| 6,309,655 B1 * | 10/2001 | Minnix | 424/401 |
| 6,310,014 B1 * | 10/2001 | Rau | 510/108 |
| 6,946,413 B2 | 9/2005 | Lange et al. | |
| 6,958,103 B2 | 10/2005 | Anderson et al. | |
| 6,960,349 B2 | 11/2005 | Shantz et al. | |
| 7,211,249 B2 | 5/2007 | Schnittger et al. | |
| 7,214,382 B2 | 5/2007 | Shefer et al. | |
| 2002/0051798 A1 * | 5/2002 | Koike et al. | 424/401 |
| 2002/0086039 A1 | 7/2002 | Lee et al. | |
| 2003/0206940 A1 * | 11/2003 | Gott et al. | 424/443 |
| 2003/0211062 A1 | 11/2003 | Laden et al. | |
| 2004/0028711 A1 | 2/2004 | Uchida et al. | |
| 2005/0037038 A1 * | 2/2005 | Gupta | 424/401 |
| 2005/0048090 A1 * | 3/2005 | Rau | 424/401 |
| 2005/0158351 A1 | 7/2005 | Soliman et al. | |
| 2005/0169868 A1 | 8/2005 | Mohammadi et al. | |
| 2005/0265942 A1 | 12/2005 | Rajaraman et al. | |
| 2006/0008621 A1 | 1/2006 | Gusky et al. | |
| 2006/0067957 A1 | 3/2006 | Hwang et al. | |
| 2006/0110415 A1 * | 5/2006 | Gupta | 424/401 |
| 2007/0099812 A1 | 5/2007 | Luizzi et al. | |
| 2007/0190014 A1 | 8/2007 | Ide et al. | |
| 2007/0207174 A1 | 9/2007 | Pluyter et al. | |
| 2008/0038360 A1 * | 2/2008 | Zukowski et al. | 424/490 |
| 2008/0132438 A1 * | 6/2008 | Hoffman et al. | 510/380 |
| 2009/0017080 A1 * | 1/2009 | Tanner et al. | 424/401 |
| 2009/0072189 A1 * | 3/2009 | Wong et al. | 252/70 |

FOREIGN PATENT DOCUMENTS

| | | |
|---|---|---|
| JP | 2002193781 | 7/2002 |
| WO | 200203952 A2 | 1/2002 |

OTHER PUBLICATIONS

International Search Report and Written Opinion, PCT/IB2009/052621 (Jan. 13, 2010).

* cited by examiner

*Primary Examiner*—Charles I Boyer
(74) *Attorney, Agent, or Firm*—Armstrong Teasdale LLP

(57) ABSTRACT

The present disclosure is directed to a cleanser including a balance of components for providing consumers with an enhanced exfoliation experience that smoothes skin immediately and sustains the smooth feeling for an extended period of time. Additionally, the cleanser provides a simultaneous cleansing and warming effect to the consumer's skin. Particularly, in one embodiment, the cleanser includes a combination of a water soluble carrier, a warming agent, a water soluble silicone surfactant, and an exfoliant.

17 Claims, No Drawings

POLYSENSORIAL PERSONAL CARE CLEANSER COMPRISING A QUATERNARY SILICONE SURFACTANT

BACKGROUND OF THE DISCLOSURE

The present disclosure is directed to a cleanser including a balance of components for providing consumers with an enhanced exfoliation experience that smoothes skin immediately and sustains the smooth feeling for an extended period of time. Additionally, the cleanser provides a simultaneous cleansing and warming effect to the consumer's skin. Particularly, in one embodiment, the cleanser includes a combination of a water soluble carrier, a warming agent, a water soluble silicone surfactant for cleansing, and an exfoliant.

Today's market includes many existing products and formulations that achieve improved skin appearance and feel by removing or exfoliating the upper layers of the epidermis, which typically contains dead skin cells. Removal of these skin cells can provide a more vital, youthful appearance to the skin while imparting a smooth, supple feel. Generally, cosmetic formulations achieve this smoothing effect by the use of physical and chemical exfoliating agents. Particularly, physical exfoliating agents include particulates that are either natural or synthetic in origin and work by abrading the skin and resurfacing the top layers. The overall use level, mean particle size, distribution, and general morphology of the particulates will determine the degree of exfoliating and feel during the exfoliation process. Alternatively, chemical exfoliating agents provide an exfoliating effect by breaking bonds within the skin to create a smooth feel. Generally, these conventional exfoliating agents can be irritating to the skin and the benefits achieved are short lived, as environmental stresses and biological processes increase skin roughness.

Other products may comprise warming agents, which warm by a positive heat of hydration as water is added to the product. Such warming products, however, typically require an anhydrous base in order to prevent premature release of heat from the warming agent. Such bases can be oily and have an unpleasant aesthetic feel.

Some of these warming products may further include surfactants for cleansing. Traditional surfactants, however, have inherent problems in anhydrous formulations. Because of the anhydrous nature of warming products, it is often necessary to include in the formulations surfactants which foam well, but which have a high irritation rate, since these surfactants are necessary to generate sufficient amounts of foam. While such surfactants foam effectively, they also carry a high likelihood of irritation to the consumer's skin. Additionally, these surfactants increase the likelihood of stripping essential oils form the consumer's skin, leaving the skin dry, tight, and unpleasant to the touch. Both the elevated irritation potential and undesirable skin feel inherent to these types of formulations are of particular concern for facial care products.

It would therefore be desirable to provide a polysensorial formulation that combines multiple benefits in a non-irritating, aesthetically pleasing cleanser and that provides both an immediate and sustained skin smoothing effect. Additionally, it would be advantageous if the cleanser could further provide cleansing and warming benefits to the skin. The present disclosure describes such a substantially anhydrous cleanser and includes: a water soluble carrier; an exfoliant; a warming agent; and a water soluble silicone surfactant.

SUMMARY OF THE DISCLOSURE

The present disclosure is directed to a personal care cleanser including a balance of components for providing consumers with an enhanced exfoliation experience that smoothes skin immediately and sustains the smooth feeling for an extended period of time. Additionally, the personal care cleanser provides a simultaneous cleansing and warming effect to the consumer's skin. Particularly, in one embodiment, the personal care cleanser includes a combination of a water soluble carrier, a warming agent, a water soluble silicone surfactant for cleansing, and an exfoliating agent.

In one aspect, the present disclosure is directed to a personal care cleanser comprising a water soluble carrier, an exfoliant, a warming agent, and a water soluble silicone surfactant, wherein the cleanser is substantially anhydrous.

In another aspect, the present disclosure is directed to a wipe comprising a fibrous wipe substrate, and a substantially anhydrous cleanser, the substantially anhydrous cleanser comprising a water soluble carrier, an exfoliant, a warming agent, and a water soluble silicone surfactant.

In another aspect, the present disclosure is directed to a skin smoothing article comprising a substrate comprising a skin-contacting surface, and a substantially anhydrous cleanser coated on the skin-contacting surface of the substrate, the substantially anhydrous cleanser comprising water soluble carrier, an exfoliant, a warming agent, and a water soluble silicone surfactant.

Other objects and features will be in part apparent and in part pointed out hereinafter.

DETAILED DESCRIPTION OF THE DISCLOSURE

The present disclosure is directed to a personal care cleanser including a balance of components for providing consumers with an enhanced exfoliation experience that smoothes skin immediately and sustains the smooth feeling for an extended period of time. Additionally, the personal care cleanser provides a simultaneous cleansing and warming effect to the consumer's skin. Particularly, in one embodiment, the personal care cleanser is a substantially anhydrous cleanser comprising a combination of a water soluble carrier, a warming agent, a water soluble silicone surfactant for cleansing, and an exfoliating agent.

The personal care cleansers of the present disclosure may be used as a warming and exfoliating facial cleanser, hand cleanser, foot cleanser or scrub, body cleanser, and the like. In certain embodiments, the cleanser may also be incorporated into a wipe to form a cleansing wipe, or may be incorporated into other skin soothing articles, such as face masks, gloves, socks, and the like. Advantageously, the cleansers provide both an immediate and long-lasting smooth feel on the skin of the user. Additionally, the presence of the warming agent in the cleanser warms the skin and relaxes pores, allowing for better removal of dirt, oils, and sebum from the skin.

The cleansers of the present disclosure will foam and produce a warming sensation on the skin of the user when contacted with water. In order to prevent premature foaming and/or release of heat by the warming agent, the cleansers of the present disclosure are substantially anhydrous. As used herein, "substantially anhydrous" is intended to mean the cleanser comprises water in an amount of about 5% (by weight of the cleanser) or less. Preferably, water is present in the cleanser in an amount of about 1% (by weight of the cleanser) or less, and more preferably about 0.5% (by weight of the cleanser) or less. More preferably, the cleanser is anhydrous (i.e., comprises 0% (by weight of the cleanser) of water). The substantially anhydrous nature of the cleansers prevents the warming agents from releasing heat until the cleanser is contacted with water.

As noted above, the cleanser of the present disclosure comprises a water-soluble carrier. Typically, any water-soluble carrier known in the cleanser arts can be used. Non-limiting examples of suitable water-soluble carrier materials include, but are not limited to, emollients, sterols or sterol derivatives, viscosity enhancers, rheology enhancers, polyols, surfactants, alcohols, esters, silicones, clays, starch, cellulose, and other pharmaceutically acceptable carrier materials. Particularly preferable water soluble carriers include glycerin, glycerin derivatives, glycols, such as polyethylene glycols and derivatives thereof, polypropylene glycols, propylene glycol, butylene glycol, ethoxydiglycol, and the like, and combinations thereof. Preferably, the water soluble carrier is a glycol. Further examples of suitable water soluble carriers include those described in CTFA, International Cosmetic Ingredient Dictionary and Handbook, 12th Ed. (2008), which is hereby incorporated by reference to the extent that it is consistent herewith.

As will be recognized by one skilled in the art, the relative amounts of such carriers in the cleansers of the disclosure will be dictated by the nature of the cleanser. The levels of carrier can be determined by routine experimentation in view of the disclosure provided herein, and may be present in the cleanser in amounts of from about 0.01% (by weight of the cleanser) to about 99% (by weight of the cleanser) and more desirably from about 0.1% (by weight of the cleanser) to about 95% (by weight of the cleanser).

As noted above, the cleansers of the present disclosure advantageously comprise a water-soluble silicone surfactant. Inclusion of a water-soluble silicone surfactant in the cleanser results in a reduction of the inherently unpleasant, oily, aesthetic feel typically associated with anhydrous compositions. Additionally, the water-soluble silicone surfactants act to remove and emulsify excessive oil from the skin, while also imparting a soft, long-lasting, perceivably smooth film onto the skin following washing with the cleanser.

Specifically, as discussed above, exfoliants, such as those included in the cleansers of the present disclosure, act to impart an immediate smooth sensation on the skin of the user. However, this smooth sensation is generally short lived, as environmental stresses and biological processes progressively increase skin roughness. It has now been discovered that inclusion of a water soluble silicone surfactant in the exfoliating cleanser extends the period of time during which the cleanser's user perceives skin smoothness. Without wishing to be bound to any particular theory, it is believed that the ethoxylation of the silicone surfactant results in production of a creamy foam when the cleanser is combined with water. After washing, the user feels immediate smoothness due to the presence of the exfoliating particles. Additionally, after using the cleanser, a deposit of silicone is left on the skin of the user, resulting in a long-term smooth feel of the skin.

The silicone surfactants included in the cleansers of the present disclosure are advantageously water soluble. As noted above, the cleansers of the present disclosure comprise a hydrophilic, water soluble carrier. Unlike other hydrophobic silicone-containing compounds, the silicone surfactants of the present disclosure are water soluble, and are thus stable in the hydrophilic carrier used in the cleansers of the present disclosure. As such, a sufficient amount of silicone surfactant can stably be included in the cleansers to impart the desired skin feel, while also not adversely impacting the quality of the foam produced by the cleanser.

In one embodiment, the water soluble silicone surfactant of the present disclosure has the following structure:

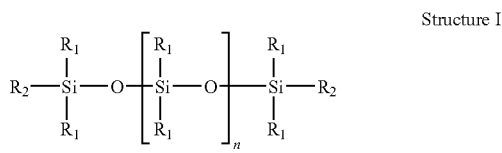

Structure I wherein each $R_1$ is independently selected from the group consisting of $CH_3$, $CH_2CH_3$, $CH_2CH_2CH_3$, $C_6H_5$, $C_4$ to $C_{30}$ alkyl chain, substituted phenyl, and naphthyl; each $R_2$ is independently selected from the group consisting of nonionic functional groups, anionic functional groups, zwitterionic functional groups, and cationic functional groups; and n is from 1 to about 2500.

Examples of suitable nonionic functional groups include: $CH_2CH_2OH$, $CH_2CH(CH_3)OH$, $(CH_2CH_2O)_bH$, $(CH_2CH(CH_3)O)_aH$, $(CH_2CH_2O)_b(CH_2CH(CH_3)O)_aH$, $(CH_2CH_2O)_b$, $(CH_2CH(CH_3)O)_a(CH_2CH_2O)_xH$, and $(CH_2CH(CH_3)O)_a(CH_2CH_2O)_bH(CH_2CH(CH_3)O)_yH$, wherein a is 1 to 50, b is 1 to 50, x is 1 to 50, and y is 1 to 50.

Examples of suitable anionic functional groups include: —$R_3$-sulfosuccinate, —$R_3$-carboxylate, —$R_3$-taurate, —$R_3$-sulfate, —$R_3$-sulfonate, —$R_3$-phosphate, sulfate (—$OSO_3^-$), isethionate (—$C(O)OCH_2CH_2SO_3^-$), sarcosinate (—$C(O)N(CH_3)CH_2CO_2^-$), sulfosuccinate (—$OC(O)CH_2CH(SO_3^-)CO_2^-$), taurate (—$C(O)N(H)CH_2CH_2SO_3^-$), phosphate (e.g., —$OP(O)(OH)O^-$, —$OP(O)(OR)O^-$), and alkylamido alkylamines such as —$R_3$—$C(O)NHCH_2CH_2N(R_4)CH_2CH_2OCH_2CO_2^-$; wherein $R_3$ is selected from the group consisting of $CH_2CH_2$, $CH_2CH_2CH_2$, $OCH_2CH_2$, $OCH_2CH_2O$, $OCH_2CH_2CH_2$, $CH_2CH_2CH_2O$, $OCH_2CH(CH_3)O$, $O(CH_2CH_2O)_b$, $O(CH_2CH(CH_3)O)_a$, $(CH_2CH_2O)_b(CH_2CH(CH_3)O)_a$; $R_4$ is selected from the group consisting of H, $CH_2CO_2^-$, $CH_2CH_2CO_2^-$, $CH_2CH(OH)CH_2SO_3^-$, and $CH_2CH(OH)CH_2OP(O)O_2H^-$; a is 1 to 50; and b is 1 to 50.

Examples of suitable zwitterionic functional groups include betaines, such as —$N(CH_3)_2CH_2CO_2^-$, and amine oxides, such as —$R_3$—$N^+(CH_3)_2$—O, wherein $R_3$ is as defined above.

In some embodiments, the water soluble silicone surfactants can contain an overall positive charge to the molecule. Water soluble silicone surfactants having an overall positive charge advantageously enhance the substantivity of the cleanser to the user's skin; i.e., improve deposit of the cleanser on the skin. Specific, nonlimiting examples of water soluble silicone surfactants having an overall positive charge include: Quaternium-80 (Abil Quat 3272 and 3474 from Evonik Care & Surface Specialties), Quaternium 86 (Pecosil SWQ-40), PEG-8 Distearmonium Chloride PG-Dimethicone, Silicone Quaternium-1, Silicone Quaternium-2, Silicone Quaternium-2 Panthenol Succinate, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-16/Glycidoxy Dimethicone Crosspolymer, Silicone Quaternium-17, Silicone Quaternium-18, Silicone Quaternium-19, Silicone Quaternium-20, Silicone Quaternium-21, Dimethicone Hydroxypropyl Trimonium Chloride, Hydroxyethyl Acetomonium PG-Dimethicone, Stearalkonium Dimethicone PEG-8 Phthalate, Steardimonium Hydroxypropyl Panthenyl PEG-7 Dimethicone Phosphate Chloride, and combinations thereof. In these embodiments, one or more $R_2$ may be a cationic functional group, such as any of those used to form the positively charged water soluble silicone surfactants listed above.

In another embodiment, the water soluble silicone surfactant of the present disclosure has the following structure:

Structure II

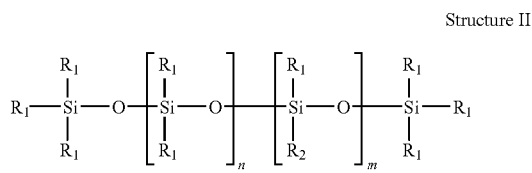

wherein $R_1$ and $R_2$ are as defined above, m is from 1 to about 2500, and n is from 1 to about 2500.

Other specific examples of suitable water soluble silicone surfactants include, but are not limited to, disodium PEG-12 dimethicone sulfosuccinate (available from McIntyre Group, Ltd. under the tradename Mackanate DC-100), and PEG-12 dimethicone, PEG-10 dimethicone, PEG-8 dimethicone, PEG-7 dimethicone, PEG-7 dimethicone succinate (all available from SilTech, LLC), and combinations thereof. Other examples of suitable water soluble silicone surfactants include PEG-20/PPG-6 dimethicone, PEG-14/PPG-4 dimethicone, PEG-4/PPG-12 dimethicone, PEG-20/PPG-20 dimethicone (available from Evonik), dimethylsiloxane and methyl(polyoxyethylene)siloxane copolymers (available from Shin Etsu Silicones), dimethylsiloxane and methyl (polyoxyethylene)siloxane and methyl(polyoxypropyl)siloxane copolymers (available from Shin Etsu Silicones), and combinations thereof. Other examples of suitable water soluble silicone surfactants include those available from Momentive Performance Materials under the name SIL-SOFT, including, for example, PEG-8 trisiloxane PEG-8/PPG-26 dimethicone, PEG-20/PPG-23 dimethicone, PEG-20/PPG-15 dimethicone, PEG-23/PPG-6 dimethicone, PEG-17 dimethicone, PPG-12 dimethicone, and the like.

Typically, the cleansers will comprise water soluble silicone surfactant in an amount of about 0.1% (by weight of the cleanser) to about 40% (by weight of the cleanser), more preferably in an amount of about 1% (by weight of the cleanser) to about 30% (by weight of the cleanser), and still more preferably in an amount of about 2% (by weight of the cleanser) to about 20% (by weight of the cleanser).

In some embodiments, the cleanser may optionally further comprise an additional surfactant, such as a non-silicone based surfactant. The non-silicone based surfactant contributes to the overall cleansing and emulsification properties of the cleanser. Many non-silicone based surfactants, while having good cleansing and foaming properties, are also harsh and irritating to the skin, and may not have desirable viscosity or suspending characteristics. Advantageously, it has now been discovered that by using a blend of the water soluble silicone surfactant of the present disclosure and a non-silicone based surfactant, a cleanser having a viscosity and thickness with good suspending, skin feel, and performance characteristics can be achieved. Additionally, because the water soluble silicone surfactants of the present disclosure are mild, they act to substantially lower the irritation potential of traditional, more irritating surfactants. Thus, by using a blend of water soluble silicone surfactant and non-silicone based foaming surfactants, the level and type of foam produced, as well as the rinsing and overall cleansing characteristics of the cleanser can be controlled, while ensuring the cleanser remains non-irritating. Ensuring control over the viscosity and lowering the overall irritation potential of the cleanser is particularly important for facial care products for ease of application around mucous membranes such as the eyes.

Any one of a number of surfactant types can be utilized as the non-silicone based surfactant of the cleanser. One skilled in the art will recognize, based on the disclosure herein, that different cleanser combinations, and particularly, the different silicone surfactants in the cleanser combinations, may benefit from one type of non-silicone based surfactant more than another; that is, the preferred non-silicone based surfactant for one chemistry may be different than the preferred non-silicone based surfactant for another. Particularly desirable non-silicone based surfactants will allow the cleanser to have a suitable viscosity for thorough mixing; that is, the non-silicone based surfactant will not result in the mixture having an undesirably high viscosity. Preferably, the cleanser will have a viscosity of at least about 30,000 cps. More preferably, the cleanser will have a viscosity of about 60,000 cps to about 600,000 cps.

As such, suitable non-silicone based surfactants may include any non-silicone based surfactant known in the art that will achieve the desired consistency and stability of the cleanser. Nonionic surfactants, anionic surfactants, cationic surfactants, betaines, sultaines, amphoteric surfactants, zwitterionic surfactants, imidazolines, sulfosuccinates, amine oxides, alkanolamides, and combinations thereof may all be suitable for use as non-silicone based surfactants in the cleanser of the present disclosure. Particularly preferred non-silicone based surfactants are sulfosuccinates and amine oxides.

Nonionic surfactants typically have a hydrophobic base, such as a long chain alkyl group or an alkylated aryl group, and a hydrophilic chain comprising a certain number (e.g., 1 to about 30) of ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and mixtures thereof.

Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty (C-$C_{22}$) alcohol, including 3 to 20 ethylene oxide moieties, polyoxyethylene-20 isohexadecyl ether, polyoxyethylene-23 glycerol laurate, PEG 80 sorbitan laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

Additional nonionic surfactants that can be used include water soluble alcohol ethylene oxide condensates, such as the condensation products of a secondary aliphatic alcohol containing between about 8 to about 18 carbon atoms in a straight or branched chain configuration condensed with between about 5 to about 30 moles of ethylene oxide. Such nonionic surfactants are commercially available under the trade name Tergitol from Union Carbide Corp., Danbury, Conn. Specific examples of such commercially available nonionic surfactants of the foregoing type are $C_{11}$-$C_{15}$ secondary alkanols condensed with either 9 moles of ethylene oxide (Tergitol 15-S-9) or 12 moles of ethylene oxide (Tergitol 15-S-12) marketed by Union Carbide Corp., (Danbury, Conn.).

Other suitable nonionic surfactants include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl condensed with about 9.5 moles of ethylene oxide per mole of nonyl phenol, dinonyl phenol condensed with about 12 moles of ethylene oxide per mole of phenol, dinonyl phenol condensed with about 15 moles of ethylene oxide per mole of phenol and diisoctylphenol condensed with about 15 moles of ethylene oxide per mole of phenol. Commercially available nonionic surfactants of this type include Igepal CO-630 (a nonyl phenol ethoxylate) marketed by ISP Corp. (Wayne, N.J.). Suitable non-ionic ethoxylated octyl and nonyl phenols include those having from about 7 to about 13 ethoxy units. Such compounds are commercially available under the trade name Triton X (Union Carbide, Danbury, Conn.).

Alkyl polyglycosides may also be used as a nonionic surfactant in the present cleansers. Suitable alkyl polyglycosides are known nonionic surfactants that are alkaline and electrolyte stable. Alkyl mono and polyglycosides are prepared generally by reacting a monosaccharide, or a compound hydrolyzable to a monosaccharide with an alcohol such as a fatty alcohol in an acid medium.

One example of such alkyl polyglycosides is APG™ 325 CS GLYCOSIDE, which is described as being a 50% C9-C11 alkyl polyglycoside, also commonly referred to as D-glucopyranoside. Another example of an alkyl polyglycoside surfactant is GLUCOPON™ 625 CS, which is described as being a 50% $C_{10}$-$C_{16}$ alkyl polyglycoside, also commonly referred to as a D-glucopyranoside. Both APG™ 325 CS GLYCOSIDE and GLUCOPON™ 625 CS are commercially available from Henkel Corp., Ambler, Pa.

Other useful nonionic surfactants include compositions based on amine oxides. One general class of useful amine oxides include alkyl di(lower alkyl)amine oxides in which the alkyl group has about 10-20, and preferably 12-16 carbon atoms, and can be straight or branched chain, saturated or unsaturated. The lower alkyl groups include between 1 and 7 carbon atoms. Examples include lauryl, dimethyl amine oxide, myristyl dimethyl amine oxide, and those in which the alkyl group is a mixture of different amine oxide, dimethyl cocoamine oxide, dimethyl (hydrogenated tallow)amine oxide, and myristyl/palmityl dimethyl amine oxide.

Another class of useful amine oxides include alkyl di(hydroxy lower alkyl)amine oxides in which the alkyl group has about 10-20, and particularly 12-16 carbon atoms, and can be straight or branched chain, saturated or unsaturated. Examples are bis(2-hydroxyethyl)cocoamine oxide, bis(2-hydroxyethyl)tallow amine oxide, and bis(2-hydroxyethyl) stearylamine oxide. Moreover, still other useful amine oxides include those characterized as alkylamidopropyl di(lower alkyl)amine oxides, in which the alkyl group has about 10-20 carbon atoms, and can be straight or branched chain, saturated or unsaturated. Examples are cocoamidopropyl dimethyl amine oxide and tallowamidopropyl dimethyl amine oxide.

Additional useful amine oxides include alkylmorpholine oxides in which the alkyl group has about 10-20 carbon atoms, and can be straight or branched chain, saturated or unsaturated. Further examples of amine oxides include those that commercially under the trade name AMMONYX (Stepan Co., Chicago, Ill.).

In addition to nonionic surfactants, the cleanser may also contain other types of surfactants. For instance, in some embodiments, amphoteric surfactants, such as zwitterionic surfactants, may also be used. For instance, one class of amphoteric surfactants that may be used in the present disclosure are derivatives of secondary and tertiary amines having aliphatic radicals that are straight chain or branched, wherein one of the aliphatic substituents contains from about 8 to 18 carbon atoms and at least one of the aliphatic substituents contains an anionic water-solubilizing group, such as a carboxy, sulfonate, or sulfate group. Some examples of amphoteric surfactants include, but are not limited to, sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine.

Additional classes of suitable amphoteric surfactants include phosphobetaines and the phosphitaines. For instance, some examples of such amphoteric surfactants include, but are not limited to, sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl) carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, di-sodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium lauryl sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, cocamidopropyl betaine, lauric myristic amido propyl monosodium phosphitaine, and mixtures thereof.

In certain instances, it may also be desired to utilize one or more anionic surfactants within the cleansers. Suitable anionic surfactants include, but are not limited to, alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylauryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof.

Particular examples of some suitable anionic surfactants include, but are not limited to, $C_8$-$C_{18}$ alkyl sulfates, $C_8$-$C_{18}$ fatty acid salts, $C_8$-$C_{18}$ alkyl ether sulfates having one or two moles of ethoxylation, $C_8$-$C_{18}$ alkamine oxides, $C_8$-$C_{18}$ alkoyl sarcosinates, $C_8$-$C_{18}$ sulfoacetates, $C_8$-$C_{18}$ sulfosuccinates, $C_8$-$C_{18}$ alkyl diphenyl oxide disulfonates, $C_8$-$C_{18}$ alkyl carbonates, $C_8$-$C_{18}$ alpha-olefin sulfonates, methyl ester sulfonates, and blends thereof. The $C_8$-$C_{18}$ alkyl group can be straight chain (e.g., lauryl) or branched (e.g., 2-ethylhexyl). The cation of the anionic surfactant can be an alkali metal (e.g., sodium or potassium), ammonium, $C_1$-$C_4$ alkylammonium (e.g., mono-, di-, tri), or $C_1$-$C_3$ alkanolammonium (e.g., mono-, di-, tri).

Specific examples of such anionic surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and similar surfactants.

Cationic surfactants, such as cetylpyridinium chloride and methylbenzethonium chloride, may also be utilized.

The cleanser may comprise non-silicone based surfactant in an amount of from about 0.1% (by weight of the cleanser) to about 40% (by weight of the cleanser), and more preferably in an amount of from about 0.1% (by weight of the cleanser) to about 20% (by weight of the cleanser), and still more preferably in an amount of from about 0.1% (by weight of the cleanser) to about 10% (by weight of the cleanser). Preferably, however, the total amount of surfactant; that is, the amount of water soluble silicone surfactant and non-silicone based surfactant included within the cleanser is generally from about 0.1% (by weight cleanser) to about 40% (by weight cleanser). More desirably, the total amount of surfactant in the cleanser is from about 1.0% (by weight cleanser) to about 30% (by weight cleanser).

Preferably, the ratio of water soluble silicone surfactant to non-silicone based surfactant in the cleanser is from about 10:1 to about 1:8, and more preferably is from about 2:1 to about 1:8.

As noted above, in addition to the water soluble silicone based surfactant, the cleansers of the present disclosure further comprise an exfoliant. The presence of dead skin cells on the skin surface can lead to rough and flaky skin, as well as the appearance of wrinkles and other undesirable effects of skin ageing. To improve these skin conditions, the cleansers of the present disclosure incorporate exfoliating agents, which act to remove dead skin cells from the upper layers of the epidermis. Removal of these cells results in a more vital, youthful appearance to the skin, while also imparting a smooth, supple skin feel.

Exfoliants suitable for use in the cleansers of the present disclosure may be physical exfoliants, chemical exfoliants, or combinations thereof. Physical and chemical exfoliants typically work by two different mechanisms. In particular, chemical exfoliants act by breaking bonds within the skin, specifically by breaking bonds of the squames (dead skin cells), resulting in a smoother skin feel. In contrast, physical exfoliants work by abrading the skin to physically slough off the layer of dead skin cells where the bond of the squames has already broken down.

Examples of suitable physical exfoliants are well known in the art, and include any suitable abrasive agent. Specific examples include, but are not limited to, olive stone, jojoba meal, bran, wheat flour grains, almond meal, corn meal, oatmeal, rice, walnut shell powder, ground bamboo, jade powder, salts, solid crystalline sugars, acetal resins, aluminum oxide, boron carbide, calcium carbonate, calcium phosphate, calcium silicate, diatomaceous earth, resins of polyamide, polyethylene, polytetrafluoroethylene, polypropyene, polyurethane, silica, pumice, quartz, silicon nitride, silicon carbide, titanium dioxide, ground fruit seeds, and other finely ground wood, shells, nut shells, nuts, and grains, and other polyolefin based powders and polytetrafluorine powders. Other examples of suitable exfoliants include those listed in CTFA, International Cosmetic Ingredient Dictionary and Handbook, 12th Ed. (2008), which is hereby incorporated by reference to the extent that it is consistent herewith.

Typically, the physical exfoliant will have a particle size of from about 50 μm to about 500 μm, and more typically about 100 μm to about 300 μm. In certain embodiments, the particle size of the physical exfoliant may be larger than 500 μm, depending on the desired degree of roughness of the cleanser against the skin.

The cleansers may comprise the physical exfoliant in an amount of from about 0.1% (by weight of the cleanser) to about 30% (by weight of the cleanser) of physical exfoliant, and preferably from about 1% (by weight of the cleanser) to about 20% (by weight of the cleanser).

Examples of suitable chemical exfoliants include, but are not limited to, alpha-hydroxy acids, beta-hydroxy acids, poly-hydroxy acids, aromatic hydroxyacids, amino sugars, and combinations thereof. Specific examples of suitable alpha-hydroxy acids include citric acid, malic acid, glycolic acid, lactic acid, and the like. Examples of suitable beta-hydroxy acids include salicylic acid, beta-hydroxy beta-methyl butyrate, carnitine, 3-hydroxypropionic acid, and the like. Examples of suitable poly-hydroxy acids include gluconolactone, glucuronolactone, gluconic acid, mannuronic acid, galactruonic acid, iduronic acid, mucic acid, and the like. Other examples of suitable chemical exfoliants include those listed in CTFA, International Cosmetic Ingredient Dictionary and Handbook, 12th Ed. (2008), which is hereby incorporated by reference to the extent that it is consistent herewith.

The amount of chemical exfoliant included in the cleanser will depend on the type of exfoliant and the strength of exfoliation desired. Typically, however, the cleansers may comprise the chemical exfoliant in an amount of from about 0.1% (by weight of the cleanser) to about 20% (by weight of the cleanser), and preferably in an amount of about 15% (by weight of the cleanser) or less.

As noted above, the cleansers of the present disclosure advantageously further comprise a warming agent. The warming agent provides the consumer with a sensory benefit by generating heat when contacted with water. For instance, the cleanser or wipe or other product containing the cleanser may be contacted with water prior to or during application to a user's skin. Release of heat by the warming agents results in a warm, pleasing feeling on the skin when the cleanser is used. Additionally, the heat produced by the warming agents may assist the surfactants present in the cleanser in releasing dirt, soil, and sebum from the skin, by relaxing and opening pores in the skin and allowing access by the surfactants.

Suitable warming agents for use in the cleanser include agents having an exothermic heat of hydration and/or an exothermic heat of solution. In particular, the warming agents will advantageously have an exothermic heat of hydration and/or an exothermic heat of solution of at least about +2 kcal/mol. More desirably, the warming agents have an exothermic heat of hydration and/or heat of solution of at least about +4 kcal/mol, more desirably of at least about +10 kcal/mol, and even more desirably of at least about +13 kcal/mol.

Examples of suitable warming agents for use in the cleanser include multivalent or metallic salts, low molecular weight glycols, neurosensory agents such as vanillyl butyl ether and capsasin, and combinations thereof.

Suitable multivalent or metallic salts for use as warming agents in the cleanser include, for example, chlorides such as calcium chloride ($CaCl_2$, $CaCl_2.H_2O$, $CaCl_2.2H_2O$) (heat of hydration of +4.9 kcal/mol), magnesium chloride ($MgCl_2$, $MgCl_2.2H_2O$, $MgCl_2.4H_2O$) (heat of hydration of +36.3 kcal/mol), aluminum chloride ($AlCl_3$, $AlCl_3.6H_2O$) (heat of hydration of +77.9 kcal/mol), ferric chloride ($FeCl_3$, $FeCl_3.2H_2O$) (heat of hydration of +31.7 kcal/mol), and zinc chloride ($ZnCl_2$); sulfates such as magnesium sulfate ($MgSO_4$, $MgSO_4.H_2O$, $MgSO_4.4H_2O$), zinc sulfate ($ZnSO_4.H_2O$), ferrous sulfate ($FeSO_4$, $FeSO_4.H_2O$), aluminum sulfate ($Al(SO_4)_3$), calcium sulfate ($CaSO_4$, $CaSO_4.½H_2O$, $CaSO_4.H_2O$), and sodium sulfate ($Na_2SO_4$); calcium oxide (CaO); magnesium oxide (MgO); sodium carbonate ($Na_2CO_3$); sodium acetate, sodium triphosphate (heat of hydration of +13 kcal/mol), potassium dihydrogen phosphate (heat of hydration of +4.7 kcal/mol), sodium hydrogenphosphate ($Na_2HPO_4$), and combinations thereof. Preferably, the warming agent is an anhydrous inorganic salt such as sodium sulfate ($Na_2SO_4$), calcium sulfate ($CaSO_4$), magnesium sulfate ($MgSO_4$), aluminum sulfate ($Al(SO_4)_3$), calcium chloride ($CaCl_2$), magnesium chloride ($MgCl_2$), calcium oxide (CaO), and combinations thereof. Particularly preferred are magnesium chloride and calcium chloride.

Suitable low molecular weight glycols for use as the warming agent include those described herein as suitable for use as the water soluble carrier. It should be noted that when a low molecular weight glycol is to be used as both the water soluble carrier and the warming agent, sufficient low molecular weight glycol should be included in the cleanser to function as both carrier and warming agent.

Other examples of suitable warming agents include zeolites, dry alum, metals, slaked lime, quick lime, sodium potassium aluminum silicate, and combinations thereof. The warming agents may be in either hydrous or anhydrous forms, although anhydrous forms are generally preferred.

The amount and type of warming agent are selected so that the cleanser is brought to a temperature sufficient to cause a warming sensation on the skin of the user when the cleanser or product containing the cleanser is contacted with water. For example, when the warming agent is a multivalent or metallic salt, the warming agent is generally included in the cleanser in an amount of from about 1.0% (by weight of the cleanser) to about 50% (by weight of the cleanser), and more desirably from about 15% (by weight of the cleanser) to about 35% (by weight of the cleanser). When the warming agent is a low molecular weight glycol, the warming agent is typically included in the cleanser in an amount of from about 0.01% (by weight of the cleanser) to about 99% (by weight of the cleanser), and more desirably from about 0.1% (by weight of the cleanser) to about 90% (by weight of the cleanser). Additionally, when the warming agent is a neurosensory agent such as vanillyl butyl ether or capsasin, the warming agent is included in an amount of from about 0.1% (by weight of the cleanser) to about 10% (by weight of the cleanser), and more desirably from about 0.1% (by weight of the cleanser) to about 1.0% (by weight of the cleanser).

The warming agent utilized in the cleanser generally has a particle size of from about 0.05 micrometers to about 4000 micrometers, desirably from about 10 micrometers to about 1000 micrometers, desirably from about 10 micrometers to about 500 micrometers, and more desirably from about 10 micrometers to about 100 micrometers to facilitate substantial and continuous heat release. In one specific embodiment, a particle size of from about 149 micrometers to about 355 micrometers is preferred. Although many warming agents as described herein are commercially available in a number of particle sizes, it will be recognized by one skilled in the art that any number of techniques can be used to grind and produce the desired particle sizes. In general, the smaller the particle size, the faster a warming sensation will be perceived by a user.

Preferably, the cleanser will warm to a temperature of from about 30° C. to about 40° C. (86° F.-104° F.), upon contact with water. A conventional cleanser is typically stored at room temperature (about 23° C. (73.4° F.)). As such, when the warming agent contacts an aqueous solution (such as water during the cleansing process), a warming sensation is produced, increasing the temperature of the cleanser by at least about 5° C. More suitably, the temperature of the cleanser is increased by at least about 10° C., even more suitably, increased by from about 10° C. to about 15° C.

Generally, the warming agent begins to generate heat and a warming sensation once contacted with water in less than about 20 seconds. More suitably, the warming sensation is perceived in less than about 10 seconds, even more suitably, in less than about 5 seconds, and even more suitably, in less than about 2 seconds.

Additionally, once the warming sensation begins, the warming sensation of the cleanser is suitably maintained for at least about 5 seconds. More suitably, the warming sensation is maintained for at least about 8 seconds, even more suitably for at least about 15 seconds, even more suitably for at least about 20 seconds, even more suitably for at least about 40 seconds, and even more suitably for at least about 1 minute.

In one embodiment, the warming agent may optionally be encapsulated. Encapsulating the warming agent prevents it from prematurely reacting with water, such as water that may be present in high humidity environments, to release heat. Additionally, by encapsulating the warming agent, the longevity of the warming sensation may be increased, since not all of the warming agent will react with water upon initial contact of the cleanser with water.

Typically, the encapsulation material comprises a polymeric material, a crosslinked polymeric material, a metal, a ceramic or a combination thereof, and results in a shell material that may be formed around the warming agent during manufacturing. Specifically, suitable encapsulation materials may include cellulose-based polymeric materials (e.g., cellulose, hydroxypropyl methylcellulose, ethyl cellulose, hydroxyethylcellulose, xanthan gum, chitosan), carbohydrate-based small molecules (e.g., lactose, mannitol, xylitol, and other sugars), polyglycolic acid, polylactic acid, and lactic acid-based aliphatic polyesters, and materials derived therefrom (e.g., dextrins and cyclodextrins) as well as other materials compatible with human tissues.

The encapsulation material typically will have a thickness of from about 0.1 micrometers to about 500 micrometers, desirably from about 1 micrometer to about 100 micrometers, more desirably from about 1 micrometer to about 50 micrometers, more desirably from about 1 micrometer to about 20 micrometers, and even more desirably from about 10 micrometers to about 20 micrometers. At these thicknesses, the cross-linked polymeric layer has a sufficient thickness to prevent the warming agent from prematurely reacting with water, while still being easily ruptured to release the warming agent upon use of the cleanser. The encapsulation material may form one discrete layer, or may be comprised of multiple layers. Suitable methods for measuring the thickness of the encapsulation layer (once fractured), and the other optional layers described herein, include Scanning Electron Microscopy (SEM) and Optical Microscopy.

Optionally, the cleansers may further comprise rheology modifiers. The rheology modifiers help the cleanser to maintain a high viscosity at elevated temperatures, such as those encountered during storage and transportation.

Suitable rheology modifiers include combinations of alpha-olefins and styrene alone or in combination with mineral oil or petrolatum, combinations of di-functional alpha-olefins and styrene alone or in combination with mineral oil or petrolatum, combinations of alpha-olefins and isobutene alone or in combination with mineral oil or petrolatum, ethylene/propylene/styrene copolymers alone or in combination with mineral oil or petrolatum, butylene/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, and stearalkonium hectorite, styrene/butadiene/styrene copolymers, styrene/isoprene/styrene copolymers, styrene-ethylene/butylene-styrene copolymers, styrene-ethylene/propylene-styrene copolymers, (styrene-butadiene) n polymers, (styrene-isoprene) n polymers, styrene-butadiene copolymers, and styrene-ethylene/propylene copolymers and combinations thereof. Specifically, rheology enhancers such as mineral oil and ethylene/propylene/styrene copolymers, and mineral oil and butylene/ethylene/styrene copolymers (Versagel blends from Penreco) are particularly preferred. Also, Vistanex (Exxon) and Presperse (Amoco) polymers are particularly suitable rheology enhancers.

Typically, the cleanser will comprise a rheology modifier in an amount of from about 0.01% (by weight of the cleanser) to about 20% (by weight of the cleanser), and preferably in an amount of from about 0.1% (by weight of the cleanser) to about 10% (by weight of the cleanser).

Additionally, one or more viscosity increasing agents, such as thickeners, may be added to the cleanser to increase the viscosity of the cleanser. Suitable viscosity increasing agents include clays and derivatives thereof, silicates, silicas and derivatives thereof, and combinations thereof. Suitable clays and derivatives thereof include, but are not limited to, bentonite and derivatives thereof such as quaternium-18 bentonite, hectorite and derivatives thereof such as quaternium-18 hectorite, montmorillonite, and combinations thereof. Suitable silicates include, but are not limited to, magnesium aluminum silicate, sodium magnesium silicate, lithium magnesium silicate, tromethamine magnesium aluminum silicate, and combinations thereof. Suitable silicas and derivatives thereof include, but are not limited to, silica, hydrated silica, hydrophobic silica, silica silylate, silica methyl silylate, colloidal silicone dioxide, fumed silica, and combinations thereof.

Other examples of suitable viscosity increasing agents include polyolefin resins, lipophilic/oil thickeners, ethylene/vinyl acetate copolymers, polyethylene, cetyl hydroxy ethyl cellulose, hydroxyethylcellulose, hydroxypropyl methylcellulose, hydroxypropylcellulose, other organically modified celluloses, PVP/decane copolymer, PVM/MA decadiene crosspolymer, PVP/eicosene copolymer, PVP/hexadecane copolymer, butylated PVP, carbomers, acrylic based thickeners, polyethylene glycol 600, polyethylene glycols, myristyl alcohol, cetyl alcohol, stearyl alcohol, behenyl alcohol, PEG-150 distearate, PEG-175 diisostearate, polyglyceryl-10 behenate/eicosadioate, disteareth-100 IPDI, polyacrylamidomethylpropane sulfonic acid, silicone crosspolymers, polyamide blends, and combinations thereof.

Still other optional components that may be desirable for inclusion into the cleanser of the present disclosure include those cosmetic and pharmaceutical ingredients commonly used in the skin care and cleansing industry. Examples include abrasives, absorbents, aesthetic components (fragrances, pigments, colorings/colorants), essential oils, skin sensates, astringents (e.g., clove oil, menthol, camphor, eucalyptus oil, eugenol, menthyl lactate, witch hazel distillate), anti-acne agents, anti-caking agents, antifoaming agents, antimicrobial agents, anti-oxidants, binders, biological additives, buffering agents, bulking agents, chelating agents, chemical additives, colorants, cosmetic astringents, cosmetic biocides, denaturants, drug astringents, external analgesics, film formers, opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents, skin soothing and/or healing agents (e.g., panthenol and derivatives thereof), aloe vera, pantothenic acid and derivatives thereof, allantoin, bisabolol, dipotassium glycyrrhizinate, skin treating agents, sunscreens, thickeners, and vitamins and derivatives thereof, and combinations thereof. Examples of these and other agents are disclosed in the CTFA Cosmetic Ingredient Handbook, 12th Ed. (2008), which is hereby incorporated by reference to the extent that it is consistent herewith.

The amounts of these optional components will depend on the other components used and the amounts of the other components in the cleansers as well as the desired benefits of the cleansers, and may readily be determined by one skilled in the art.

The degree of exfoliation, skin smoothing, and cleansing can also be controlled by the frequency with which the cleansers are applied to the skin. Typically, the cleansers are applied periodically for a period of time sufficient to exfoliate the skin and provide a skin smoothing benefit. For instance, in one embodiment, the cleansers are applied to the skin for a period of about 30 days to about 90, and preferably for about 60 days. In another embodiment, the cleansers are applied to the skin for a period of at least 2 months, and preferably for at least 4 months, during which time the cleansers are applied on a weekly basis. A user may also obtain the benefits of the cleanser via chronic topical application of the cleanser to exfoliate, smooth, and cleanse the skin. For example, "chronic" application may be within a range of from about once per week to about 4 to 5 times weekly, preferably daily, most preferably twice daily. By "chronic" application, it is meant herein that the period of topical application may be over the lifetime of the user, preferably for a period of at least about 6 months to about 20 years, more preferably from about 1 year to about 10 years, and still more preferably from about 2 years to about 5 years, thereby resulting in regular desquamation, which may aid in reducing the appearance of fine lines and wrinkles due to chronological aging or photoaging.

The cleanser may be applied using any suitable method. For instance, in one embodiment, the hands of a user are wetted, and the cleanser is rubbed onto the skin using the wetted hands, resulting in the production of foam and the warming of the cleanser. The foaming, warming cleanser may then be applied to any desired area of the skin of the user. For example, the cleanser may be used as a facial cleanser, a hand cleanser, a foot cleanser or exfoliating foot scrub, a body cleanser, or the like. Preferably, the cleanser is used as a warming, exfoliating facial cleanser.

In another embodiment, the cleanser is incorporated into a personal care product that may be used to apply the cleanser to skin. Examples of suitable products include a wipe, tissue, face mask, glove or mitt, glove liner, sock or bottie, wrap or patch, and the like.

In one particular embodiment, the cleanser is incorporated into a wipe. Materials suitable for the substrate of the wipes are well know to those skilled in the art, and are typically made from a fibrous sheet material which may be either woven or nonwoven. For example, suitable materials for use in the wipes may include nonwoven fibrous sheet materials which include meltblown, coform, air-laid, bonded-carded web materials, hydroentangled materials, and combinations thereof. Such materials can be comprised of synthetic or natural fibers, or a combination thereof. Typically, the wipes of the present disclosure define a basis weight of from about 25 grams per square meter to about 120 grams per square meter and desirably from about 40 grams per square meter to about 90 grams per square meter.

In one particular embodiment, the wipes of the present disclosure comprise a coform basesheet of polymer fibers and absorbent fibers having a basis weight of from about 60 to about 80 grams per square meter and desirably about 75 grams per square meter. Such coform basesheets are manufactured generally as described in U.S. Pat. No. 4,100,324, issued to Anderson, et al. (Jul. 11, 1978); U.S. Pat. No. 5,284,703, issued to Everhart, et al. (Feb. 8, 1994); and U.S. Pat. No. 5,350,624, issued to Georger, et al. (Sep. 27, 1994), which are incorporated by reference to the extent to which they are consistent herewith. Typically, such coform basesheets comprise a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, Vistamaxx® elastic olefin copolymer resin designated PLTD-1810, available from ExxonMobil Corporation (Houston, Tex.) or KRATON G-2755, available from Kraton Polymers (Houston, Tex.) may be used to provide stretchable polymeric meltblown fibers for the coform basesheets. Other suitable polymeric materials or combinations thereof may alternatively be utilized as known in the art.

As noted above, the coform basesheet additionally may comprise various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. of Federal Way (Washington); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

The relative percentages of the polymeric meltblown fibers and cellulosic fibers in the coform basesheet can vary over a wide range depending upon the desired characteristics of the wipes. For example, the coform basesheet may comprise from about 10 weight percent to about 90 weight percent, desirably from about 20 weight percent to about 60 weight percent, and more desirably from about 25 weight percent to about 35 weight percent of the polymeric meltblown fibers based on the dry weight of the coform basesheet being used to provide the wipes.

In an alternative embodiment, the wipes of the present disclosure can comprise a composite which includes multiple layers of materials. For example, the wipes may include a three layer composite which includes an elastomeric film or meltblown layer between two coform layers as described above. In such a configuration, the coform layers may define a basis weight of from about 15 grams per square meter to about 30 grams per square meter and the elastomeric layer may include a film material such as a polyethylene metallocene film. Such composites are manufactured generally as described in U.S. Pat. No. 6,946,413, issued to Lange, et al. (Sep. 20, 2005), which is hereby incorporated by reference to the extent it is consistent herewith.

In accordance with the present disclosure, the cleanser may be applied to one or both sides of the fibrous wipe substrate, or may be impregnated into the fibrous wipe substrate to form a cleansing wipe. Typically, the cleanser is applied to the wipe substrate in an amount of from about 50% (by weight of the substrate) to about 500% (by weight of the substrate, and more particularly, in an amount of from about 200% (by weight of the substrate) to about 400% (by weight of the substrate).

The wipe can be wetted with an aqueous solution just prior to, or at the point of, use of the wipe. The aqueous solution can be any aqueous solution known in the art to be suitable for use in wipe products. Generally, the aqueous solution includes mainly water, and can further include additional components, such as cleansers, lotions, preservatives, fragrances, surfactants, emulsifiers, and combinations thereof. Once the wipe is wetted with the aqueous solution and the contents of the cleanser contact the aqueous solution, the warming agent in the cleanser reacts with the aqueous solution to generate heat, resulting in a warming sensation in the wipe. Additionally, the consumer can agitate the wetted wipe, such as by rubbing it together between the hands or against other areas of the skin, to produce foam prior to or during cleansing.

In addition to wipes, the cleansers of the present disclosure may be incorporated into other articles which may be used to smooth skin, such as face masks, gloves or mitts, glove liners, socks or botties, wraps or patches, and the like. The article generally comprises an outer surface which faces away from the skin and an inner, skin-contacting surface which comes into direct contact with the skin of the wearer. The skin contacting surface of the article is coated with a cleanser of the present disclosure. As noted above, the cleanser is substantially anhydrous. Upon donning of the article, the anhydrous cleanser will contact the skin of the article's wearer. Moisture present in the skin may interact with the warming agents in the cleanser to produce a warming sensation when the article is worn. Additionally, moisture from the skin may interact with the surfactants present in the cleanser to produce a foam when the article is worn. Alternately, the article may be wetted with an aqueous solution, such as water, prior to use of the article.

The articles may comprise a nonwoven or elastomeric substrate, with the cleanser coated on a skin-contacting surface of the article in an amount of from about 50% (by weight of the substrate) to about 500% (by weight of the substrate), and more preferably in an amount of from about 200% (by weight of the substrate) to about 400% (by weight of the substrate).

When a nonwoven substrate is used with the cleanser, commercially available thermoplastic polymeric materials can be advantageously employed in making the fibers or filaments from which the substrate is formed. As used herein, the term "polymer" shall include, but is not limited to, homopolymer, copolymers, such as for example, block, graft, random and alternating copolymers, terpolymers, etc., and blends and modifications thereof. Moreover, unless otherwise specifically limited, the term "polymer" shall include all possible geometric configurations of the material, including, without limitation, isotactic, syndiotactic, random and atactic symmetries. As used herein, the terms "thermoplastic polymer" or "thermoplastic polymer material" refer to a long-chain polymer that softens when exposed to heat and returns to the solid state when cooled to ambient temperature. Exemplary thermoplastic materials include, without limitation, polyvinyl chlorides, polyesters, polyamides, polyfluorocarbons, polyolefins, polyurethanes, polystyrenes, polyvinyl alcohols, caprolactams, and copolymers thereof.

Alternatively, or in addition to the polymeric materials above, the nonwoven substrates can be prepared from cellulosic fibers. Numerous cellulosic fibers, such as, for example, wood pulp fibers or staple fibers can be used in the nonwoven substrates. Suitable commercially available cellulosic fibers for use in the nonwoven substrates can include, for example, NF 405, which is a chemically treated bleached southern softwood Kraft pulp, available from Weyerhaeuser Co. of Federal Way (Wash.); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

Nonwoven substrates can be formed by a variety of known forming processes, including airlaying, meltblowing, spunbonding, or bonded carded web formation processes. "Airlaid" refers to a porous web formed by dispersing fibers in a moving air stream prior to collecting the fibers on a forming surface. The collected fibers are then typically bonded to one another using, for example, hot air or a spray adhesive. Suitable examples of airlaid webs can be found in U.S. Pat. No. 5,486,166 to Bishop, et al., U.S. Pat. No. 6,960,349, issued to Shantz, et al. (Nov. 1, 2005), and U.S. Publication No. 2006/0008621 to Gusky, et al., all incorporated by reference to the extent that they are consistent herewith.

The fibrous nonwoven substrate material may also comprise meltblown materials. "Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface or support to form a web of randomly dispersed meltblown fibers. Such a process is disclosed, for example, in U.S. Pat. No. 3,849,241 to Butin et al. Meltblowing processes can be used to make fibers of various dimensions, including macrofibers (with average diameters from about 40 to about 100 microns), textile-type fibers (with average diameters between about 10 and 40 microns), and microfibers (with average diameters less than about 10 microns). Meltblowing processes are particularly suited to making microfibers, including ultra-fine microfibers (with an average diameter of about 3 microns or less). A description of an exemplary process of making ultra-fine microfibers may be found in, for example, U.S. Pat. No. 5,213,881 to Timmons, et al. Meltblown fibers may be continuous or discontinuous and are generally self bonding when deposited onto a collecting surface.

"Spunbonded fibers" refers to small diameter fibers which are formed by extruding molten thermoplastic material as filaments from a plurality of fine, usually circular capillaries of a spinneret with the diameter of the extruded filaments then being rapidly reduced to fibers as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al., the contents of which are incorporated herein by reference in their entirety. Spunbond fibers are generally continuous and have diameters generally greater than about 7 microns, more particularly, between about 10 and about 20 microns.

"Bonded-carded web" refers to a web made from staple fibers sent through a combing or carding unit, which separates or breaks apart and aligns the fibers to form a nonwoven web. For example, the web may be a powder bonded carded web, an infrared bonded carded web, or a through-air bonded carded web. Examples of such materials may be found in U.S. Pat. No. 5,490,846 to Ellis et al.; U.S. Pat. No. 5,364,382 to Latimer; and U.S. Pat. No. 6,958,103 to Anderson, et al.

In one particular embodiment, the nonwoven substrate is an elastomeric substrate. Elastomeric substrates are particularly useful when the substrate is to be used in a laminated article such as a glove, sock, or facemask as it is oftentimes desirable for the glove, sock, or facemask to be able to stretch to provide for easier donning. The elastomeric substrate may be formed from a natural or a synthetic latex or a dissolved elastomeric polymer, such as a thermoplastic elastomeric polyolefin polymer. For instance, the elastomeric substrate may be formed of a natural or synthetic rubber, a nitrile rubber, a nitrile butadiene rubber, a polyisoprene, a polychloroprene, a polyurethane, a neoprene, a homopolymer of a conjugated diene, a copolymer of a least two conjugated dienes, a copolymer of at least one conjugated diene and at least one vinyl monomer, styrene block copolymers, or any other suitable combinations thereof. Examples of suitable synthetic rubbers can also include acrylic diene block copolymers, acrylic rubber, butyl rubber, EPDM rubber, polybutadiene, chlorosulfonated polyethylene rubber, and fluororubber.

The elastomeric substrates (also referred to herein as films) can be formed by mixing the components together, heating and then extruding the components into a mono-layer or multi-layer substrate using any one of a variety of elastomeric film-producing processes known to those of ordinary skill in the film processing art. Such film-making processes include, for example, cast embossed, chill and flat cast, and blown film processes.

As noted above, these substrates can be used alone or can be combined to form a laminated article having at least a first substrate and a second substrate. One particularly preferred laminated article of the present disclosure will generally have 3 layers: a water-impermeable substrate, such as a film, sandwiched between two fibrous substrates, such as the nonwoven substrates described above.

While described herein as having three substrate layers, it should be recognized by one skilled in the art that the laminated article can have only two substrates bonded together or can have more than three substrate layers, such as four substrates, five substrates or even six or more substrates without departing from the present disclosure.

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

In this example, a warming exfoliating facial cleanser was prepared. The following ingredients were used to prepare the cleanser.

TABLE 1

| Trade Name | INCI Name | Amount (% w/w) |
|---|---|---|
| Phase 1 | | |
| Polyglycol 1000 | PEG-20 | 0.80 |
| Lumulse PEG 300 | PEG-6 | 21.625 |
| Propylene glycol | Propylene glycol | 21.625 |
| Germazide C | Chlorphenesin | 0.15 |
| Cosept P | Propylparaben | 0.10 |
| Crodacol 1618 | Cetaryl alcohol | 1.00 |
| Synthetic beeswax | Synthetic beeswax | 1.00 |
| Crothix | PEG-150 penterythrityl tetrastearate | 0.20 |
| Silsurf Di1010 | PEG-10 dimethicone | 1.50 |
| Phase 2 | | |
| Aerosil 300 | Silica | 3.00 |
| Phase 3 | | |
| Magnesium sulfate anhydrous | Magnesium sulfate anhydrous | 35.00 |
| Mackanate DC-100 | Disodium PEG-12 dimethicone sulfosuccinate | 5.00 |
| Mackanate CM-100F | Disodium cocamido MEA-sulfosuccinate | 5.00 |
| Phase 4 | | |
| Tagat CH40 | PEG-40 hydrogenated castor oil | 0.20 |
| Mandarin & ginger flower 178470B | Fragrance | 0.20 |
| Lipo WSF 35/60 | *Juglans regia* (walnut) shell | 1.50 |
| Rice flour RF-L00030-12 | *Oryza sativa* (rice) bran | 1.50 |
| ABS fruit mix MFA BG | Butylene glycol/*saccharum officinarum* (sugar cane) extract/*pyrus malus* (apple) fruit extract/*citrus aurantium dulcis* (orange) fruit extract/citrus *medica limonum* (lemon) fruit extract/*camellia oleifera* leaf extract | 0.20 |
| Actiphyte of papaya BG 100P | Butylene glycol/*carica papaya* fruit extract | 0.20 |
| Actiphyte of pineapple BG 100P | Butylene glycol/*ananas sativus* (pineapple) fruit extract | 0.20 |

To prepare the cleanser, the phase 1 ingredients were combined while heating to 70° C. The phase 2 ingredient was then added with moderate agitation. The phase 3 ingredients were then added, and the resulting mixture was cooled to 40° C., followed by addition of the extracts and exfoliating agents.

The fragrance was premixed with the solubilizer and then added to the cleanser formulation.

Example 2

In this example, a warming exfoliating cleanser of the present disclosure was prepared. The ingredients and amounts used to prepare the cleanser are set forth in Table 2.

TABLE 2

| Trade Name | INCI Name | Amount (% w/w) |
|---|---|---|
| Phase 1 | | |
| Polyglycol 1000 | PEG-20 | 0.80 |
| Lumulse PEG 300 | PEG-6 | 20.625 |
| Propylene glycol | Propylene glycol | 20.625 |
| Germazide | Chlorphenesin | 0.15 |
| Cosept P | Propylparaben | 0.10 |
| Crodacol 1618 | Cetaryl alcohol | 1.00 |
| Synthetic beeswax | Synthetic beeswax | 1.00 |
| Crothix | PEG-150 penterythrityl tetrastearate | 0.20 |
| Silsurf Di1010 | PEG-10 dimethicone | 1.50 |
| Phase 2 | | |
| Aerosil 300 | Silica | 3.00 |
| Phase 3 | | |
| Magnesium sulfate anhydrous | Magnesium sulfate anhydrous | 35.00 |
| Mackadet EZ-154 | Disodium lauryl sulfosuccinate/sodium $C_{14-16}$ olefin sulfonate/lauramidopropyl betaine | 12.00 |
| Phase 4 | | |
| Tagat CH40 | PEG-40 hydrogenated castor oil | 0.20 |
| Mandarin & ginger flower 178470B | Fragrance | 0.20 |
| Lipo WSF 35/60 | *Juglans regia* (walnut) shell | 1.50 |
| Rice flour RF-L00030-12 | *Oryza sativa* (rice) bran | 1.50 |
| ABS fruit mix MFA BG | Butylene glycol/*saccharum officinarum* (sugar cane) extract/*pyrus malus* (apple) fruit extract/*citrus aurantium dulcis* (orange) fruit extract/citrus *medica limonum* (lemon) fruit extract/*camellia oleifera* leaf extract | 0.20 |
| Actiphyte of papaya BG 100P | Butylene glycol/*carica papaya* fruit extract | 0.20 |
| Actiphyte of pineapple BG 100P | Butylene glycol/*ananas sativus* (pineapple) fruit extract | 0.20 |

The cleanser was prepared as described in Example 1.

Example 3

In this example, the effect of different blends of surfactants on cleanser viscosity was evaluated. Cleansers containing varying amounts of water soluble silicone surfactants, non-silicone based surfactants, or blends of water soluble silicone surfactants and non-silicone based surfactants were prepared. Specifically, the cleansers were prepared as described in Example 1, except the Mackanate CM-100F and Mackanate DC-100 from the Example 1 formulation were substituted with the surfactants and amounts of surfactant set forth in Table 3 below, and the amount of PEG-6 and propylene glycol in the Example 1 cleanser was adjusted (maintaining a 1:1 ratio), based on the amount of included surfactant. The type and amount of each surfactant, as well as viscosity and spindle size are set forth in Table 3 below.

TABLE 3

| Surfactant | Viscosity (cps) | Spindle |
| --- | --- | --- |
| 10% Mackanate CM-100F | 34,524 | TE @ 3 rpm |
| 10% Mackanate DC-100 | 1,210,000 | TF @ 0.3 rpm |
| 5% Mackanate CM-100F | 11,404 | TE @ 6 rpm |
| 5% Mackanate DC-100 | 60,600 | TE @ 3 rpm |
| 5% Mackanate CM-100F and 5% Mackanate DC-100 | 323,000 | TF @ 0.6 rpm |
| 2.5% Mackante CM-100F and 2.5% Mackanate DC-100 | 44,000 | TE @ 3 rpm |
| 12% Mackanate DC-100 | 1,370,000 | TF @ 0.3 rpm |
| 12% Mackadet EZ-154 | 519,000 | TF @ 0.6 rpm |
| 6% Mackanate DC-100 and 6% Mackadet EZ-154 | 1,050,000 | TF @ 0.3 rpm |

Mackanate DC-100 (disodium PEG-12 dimethicone sulfosuccinate), Mackanate CM-100F (disodium cocamido MEA sulfosuccinate), and Mackadet EZ-154 (disodium lauryl sulfosuccinate/sodium $C_{14-16}$ olefin sulfonate/lauramidopropyl betane) are commercially available from McIntyre Group, Ltd.

As can be seen from these results, the viscosity of the cleansers can be varied by altering the amount and type of surfactant included in the cleanser. Inclusion of 10% of the non-silicone based surfactant disodium cocamido MEA sulfosuccinate (Mackanate CM-100F) produced a relatively thin cleanser having a viscosity of about 34,524 cps, while the cleanser comprising 10% of the water soluble silicone surfactant disodium PEG-12 dimethicone sulfosuccinate (Mackanate DC-100) was thick and paste-like, having a viscosity of about 1.21 million cps. In contrast, the cleanser comprising a 5%:5% blend of water soluble silicone surfactant and non-silicone based surfactant had a cream-like viscosity that was easily squeezed from a tube and yielded good aesthetics on the skin.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above compositions and products without departing from the scope of the disclosure, it is intended that all matter contained in the above description shall be interpreted as illustrative and not in a limiting sense.

What is claimed is:

1. A personal care cleanser comprising:
   a) a water soluble carrier;
   b) a physical exfoliant having a particle size of from about 50 μm to about 500 μm;
   c) a warming agent; and
   d) a water soluble silicone surfactant selected from the group consisting of Quaternium-80, Quaternium 86, PEG-8 Distearmonium Chloride PG-Dimethicone, Silicone Quaternium-1, Silicone Quaternium-2, Silicone Quaternium-2 Panthenol Succinate, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-16/Glycidoxy Dimethicone Crosspolymer, Silicone Quaternium-17, Silicone Quaternium-18, Silicone Quaternium-19, Silicone Quaternium-20, Silicone Quaternium-21, Dimethicone Hydroxypropyl Trimonium Chloride, Hydroxyethyl Acetomonium PG-Dimethicone, Stearalkonium Dimethicone PEG-8 Phthalate, Steardimonium Hydroxypropyl Panthenyl PEG-7 Dimethicone Phosphate Chloride, and combinations thereof,
   wherein the cleanser is substantially anhydrous.

2. The cleanser of claim 1 wherein the cleanser comprises the water soluble silicone surfactant in an amount of from about 0.1% (by weight of the cleanser) to about 40% (by weight of the cleanser).

3. The cleanser of claim 1 further comprising a non-silicone based surfactant.

4. The cleanser of claim 3 wherein the non-silicone based surfactant is selected from the group consisting of sulfosuccinate and amine oxide.

5. The cleanser of claim 3 wherein the water soluble silicone surfactant and the non-silicone based surfactant are present in the cleanser in a ratio of from about 10:1 to about 1:8.

6. The cleanser of claim 1 wherein the cleanser comprises the physical exfoliant in an amount of from about 0.1% (by weight of the cleanser) to about 30% (by weight of the cleanser).

7. The cleanser of claim 1 wherein the cleanser further comprises a chemical exfoliant in an amount of from about 0.1% (by weight of the cleanser) to about 20% (by weight of the cleanser).

8. The cleanser of claim 1 wherein the warming agent is selected from the group consisting of multivalent or metallic salts, low molecular weight glycols, vanillyl butyl ether, capsasin, and combinations thereof.

9. The cleanser of claim 8 wherein the multivalent or metal salt is included in the cleanser in an amount of from about 1.0% (by weight of the cleanser) to about 50% (by weight of the cleanser).

10. The cleanser of claim 1 wherein the warming agent has a heat of hydration of at least about 2 kcal/mol.

11. The cleanser of claim 1 wherein the warming agent is encapsulated.

12. The cleanser of claim 1 wherein the water soluble carrier is selected from the group consisting of glycerin, glycerin derivatives, glycols, polyethylene glycols, polyethylene glycol derivatives, polypropylene glycols, propylene glycol, butylene glycol, ethoxydiglycol, and combinations thereof.

13. The cleanser of claim 1 wherein the cleanser has a viscosity of about 30,000 cps or greater.

14. The cleanser of claim 13 wherein the cleanser has a viscosity of about 60,000 cps to about 600,000 cps.

15. A wipe comprising:
   i) a fibrous wipe substrate, and
   ii) a substantially anhydrous cleanser, the substantially anhydrous cleanser comprising;
      a) a water soluble carrier;
      b) a physical exfoliant having a particle size of from about 50 μm to about 500 μm;
      c) a warming agent; and
      d) a water soluble silicone surfactant selected from the group consisting of Quaternium-80, Quaternium 86, PEG-8 Distearmonium Chloride PG-Dimethicone, Silicone Quaternium-1, Silicone Quaternium-2, Silicone Quaternium-2 Panthenol Succinate, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-16/Glycidoxy Dimethicone Crosspolymer, Silicone Quaternium-17, Silicone Quaternium-18, Silicone Quaternium-19, Silicone Quaternium-20, Silicone Quaternium-21, Dimethicone Hydroxypropyl Trimonium Chloride, Hydroxyethyl Acetomonium PG-Dimethicone, Stearalkonium Dimethicone PEG-8 Phthalate, Steardimonium Hydroxypropyl Panthenyl PEG-7 Dimethicone Phosphate Chloride, and combinations thereof.

16. A skin smoothing article comprising:

i) a substrate comprising a skin-contacting surface, and ii) a substantially anhydrous cleanser coated on the skin-contacting surface of the substrate, the substantially anhydrous cleanser comprising;

a) a water soluble carrier;

b) a physical extoliant having a particle size of from about 50 μm to about 500 μm;

c) a warming agent; and d) a water soluble silicone surfactant selected from the group consisting of Quaternium-80, Quaternium 86, PEG-8 Distearmonium Chloride PG-Dimethicone, Silicone Quaternium-1, Silicone Quaternium-2, Silicone Quaternium-2 Panthenol Succinate, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, Silicone Quaternium-16, Silicone Quaternium-16/Glycidoxy Dimethicone Crosspolymer, Silicone Quaternium-17, Silicone Quaternium-18, Silicone Quaternium-19, Silicone Quaternium-20, Silicone Quaternium-21, Dimethicone Hydroxypropyl Trimonium Chloride, Hydroxyethyl Acetomonium PG-Dimethicone, Stearalkonium Dimethicone PEG-8 Phthalate, Steardimonium Hydroxypropyl Panthenyl PEG-7 Dimethicone Phosphate Chloride, and combinations thereof.

17. The article of claim 16 wherein the article is selected from the group consisting of a face mask, a glove, a mitt, a sock, a glove liner, a patch, and a wrap.

* * * * *